(12) United States Patent
Yoshida et al.

(10) Patent No.: US 10,172,332 B2
(45) Date of Patent: Jan. 8, 2019

(54) METHOD FOR REGENERATING HAIR FOLLICLES USING CD36-EXPRESSING DERMAL SHEATH CELLS

(71) Applicant: Shiseido Company, Ltd., Tokyo (JP)

(72) Inventors: Yuzo Yoshida, Yokohama (JP); Tsutomu Soma, Yokohama (JP); Shigeyoshi Fujiwara, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/076,836

(22) Filed: Mar. 22, 2016

(65) Prior Publication Data

US 2016/0193140 A1   Jul. 7, 2016

Related U.S. Application Data

(62) Division of application No. 13/876,608, filed as application No. PCT/JP2010/066999 on Sep. 29, 2010, now abandoned.

(51) Int. Cl.

| A01N 63/00 | (2006.01) |
| A01N 65/00 | (2009.01) |
| C12N 5/071 | (2010.01) |
| A01K 67/027 | (2006.01) |
| A61K 35/36 | (2015.01) |
| A61L 27/38 | (2006.01) |
| A61K 8/98 | (2006.01) |
| A61Q 7/00 | (2006.01) |
| C12N 5/0775 | (2010.01) |

(52) U.S. Cl.
CPC ........ *A01K 67/027* (2013.01); *A01K 67/0271* (2013.01); *A61K 8/985* (2013.01); *A61K 35/36* (2013.01); *A61L 27/3813* (2013.01); *A61Q 7/00* (2013.01); *C12N 5/0627* (2013.01); *C12N 5/0628* (2013.01); *A01K 2207/12* (2013.01); *A01K 2227/105* (2013.01); *A01K 2267/03* (2013.01); *A61K 2800/70* (2013.01); *A61L 2430/18* (2013.01); *C12N 5/0666* (2013.01)

(58) Field of Classification Search
CPC .... A61K 35/36; C12N 5/0628; C12N 5/0666; A61L 2430/18
USPC .............................. 424/93.3, 93.7; 435/371
See application file for complete search history.

(56) References Cited

U.S. PATENT DOCUMENTS

| 7,718,426 B2 | 5/2010 | Kishimoto et al. |
| 2007/0122386 A1 | 5/2007 | Kishimoto et al. |
| 2007/0128172 A1 | 6/2007 | Yoshizato et al. |

FOREIGN PATENT DOCUMENTS

| EP | 1 437 042 A1 | 7/2004 |
| EP | 1 688 484 A1 | 8/2006 |
| EP | 1 702 632 A1 | 9/2006 |
| EP | 1 757 307 A1 | 2/2007 |
| EP | 1 950 284 A1 | 7/2008 |
| JP | 2005132813 A | 5/2005 |
| JP | 2008125540 A | 6/2008 |
| WO | 01/32840 A2 | 5/2001 |
| WO | 2005/053763 A1 | 6/2005 |
| WO | 2005/071063 A1 | 8/2005 |
| WO | 2007/037486 A1 | 4/2007 |
| WO | 2007/100870 A2 | 9/2007 |

OTHER PUBLICATIONS

Kolf et al., 2007, Arthritis Research & Therapy, vol. 9, p. 204, 10 pages.*
Alenzi et al., 2011, African Journal of Biotechnology, vol. 10(86), pp. 19929-19940.*
Rahmani et al., 2014, Developmental Cell, vol. 31, p. 543-558.*
Zhang et al., 2014, Journal of Tissue Engineering, vol. 5, p. 1-10.*
Mohammadi et al., 2016, Stem Cells and Development, vol. 25, No. 23, p. 1767-1779.*
Wu et al., 2012, Aging Research reviews, vol. 11, p. 32-40.*
Steinert et al., 2007, Arthritis Research & therapy, vol. 9, No. 3, 213, p. 1-15.*
Li et al., 2009, Transplant Immunology, vol. 21, p. 70-74.*
Sprangers et al., 2008, Kidney International, vol. 74, p. 14-21.*
S. Kurata, et al., "Viability of Isolated Single Hair Follicles Preserved at 4 Degrees Celsius," Dermatologic Surgery, vol. 25, No. 1, pp. 26-29 (1999).
T. Matsuzaki, et al., "The Upper Dermal Sheath Has a Potential to Regenerate the Hair in the Rat Follicular Epidermis," Differentiation, vol. 60, pp. 287-297 (1996).
L. Primo, et al., "Identification of CD36 Molecular Features Required for Its in Vitro Angiostatic Activity," The FASEB Journal FJ Express, vol. 19, No. 12, pp. 1713-1715 (2005).
Kishimoto, et al., "Selective Activation of the Versican Promoter by Epithelial-Mesenchymal Interactions During Hair Follicle Development," Proc. Natl. Acad. Sci. USA, vol. 96, pp. 7336-7341, (1999).
Jahoda et al., "Cellular and Extracellular Involvement in the Regeneration of the Rat Lower Vibrissa Follicle," Development, vol. 114(4), pp. 887-897, (1992).
Horne K.A. and Jahoda, C. A. B., "Restoration of Hair Growth by Surgical Implantation of Follicular Dermal Sheath", Development, vol. 116(3), pp. 563-571, (1992).
Tobin et al., "Plasticity and Cytokinetic Dynamics of the Hair Follicle Mesenchyme: Implications for Hair Growth Control," The Journal of Investigative Dermatology, vol. 120, pp. 895-904, (2003).
Lindner et al., "Involvement of Hepatocyte Growth Factor / Scatter Factor and Met Receptor Signaling in Hair Follicle Morphogenesis and Cycling," Federation of American Societies for Experimental Biology, vol. 14(2), pp. 319-332 (2000).

(Continued)

*Primary Examiner* — Shin Lin Chen

(57) ABSTRACT

Provided is a method for regenerating hair follicles by transplanting a composition containing CD36-expressing dermal sheath cells (DSc) to a human. The composition may be prepared by sorting CD36-expressing dermal sheath cells from a hair follicle tissue by use of a cell-sorting technique along with an antibody to CD36. The composition may also contain dermal papilla cells (DPc).

12 Claims, 6 Drawing Sheets

Specification includes a Sequence Listing.

(56) References Cited

OTHER PUBLICATIONS

The European Patent Office, "The Extended European Search Report," including supplementary European search report and European search opinion, issued in European Application No. 10857831.1 - 1456 / 2623106, PCT/JP2010066999, which is a European counterpart application to U.S. Appl. No. 13/876,608, dated Feb. 25, 2014.

Simon et al., "Expression of Thrombospondin-1 and the Thrombospondin-Receptor (CD36) in Healthy and Diseased Human Skin," Akteulle Dermatologie, vol. 21(6), pp. 164-166 (1995), Abstract.

Soma et al., "Microarray Analysis of Hair Inductive Signals from Dermal Papilla Cells," The Journal of Investigative Dermatology, vol. 124(4), p. A101 (2005), Abstract.

Weinberg et al., "Reconstitution of Hair Follicle Development in Vivo: Determination of Follicle Formation, Hair Growth, and Hair Quality by Dermal Cells," The Journal of Investigative Dermatology, vol. 100(3), pp. 29-236 (1993).

Yano et al., "Thrombospondin-1 Plays a Critical Role in the Induction of Hair Follicle Involution and Vascular Regression During the Catagen Phase," The Journal of Investigative Dermatology, vol. 120(1), pp. 14-19 (2003).

Machiko Iida, Setsunosuke Ihara, and Takashi Matsuzaki, "Hair cycle-dependent changes of alkaline phosphatase activity in the mesenchyme and epithelium in mouse vibrissal follicles," Develop. Growth Differ., vol. 49, 185-195 (2007).

D. Hoeller et al., "An improved and rapid method to construct skin equivalents from human hair follicles and fibroblasts," Experimental Dermatology, vol. 10, Issue 4, pp. 264-271, Aug. 2001.

Jeffrey Teumer, Ph.D. et al., "Follicular Cell Implantation: An Emerging Cell Therapy for Hair Loss," Seminars in Plastic Surgery, vol. 19, No. 2, pp. 193-200, May 2005.

Intellectual Property Office of Singapore, "Search Report" and "Written Opinion," issued in Singapore Patent Application No. 201302361-9, which is a Singapore counterpart application to U.S. Appl. No. 13/876,608, dated Jun. 17, 2014.

Marilia Cascalho et al., "Xenotransplantation and the Future of Renal Replacement", Journal of the American Society of Nephrology, vol. 15, pp. 1106-1112 (2004).

Kevin J. McElwee et al., "Cultured Peribulbar Dermal Sheath Cells Can Induce Hair Follicle Development and Contribute to the Dermal Sheath and Dermal Papilla", The Journal of Investigative Dermatology, vol. 121, No. 6, pp. 1267-1275 (Dec. 2003).

Ying Zheng et al., "Organogenesis From Dissociated Cells: Generation of Mature Cycling Hair Follicles From Skin-Derived Cells," The Journal of Investigative Dermatology, vol. 124, Issue 5, pp. 867-876, May 2005, The Society for Investigative Dermatology, Inc.

* cited by examiner

METHOD FOR REGENERATING HAIR FOLLICLES USING CD36-EXPRESSING DERMAL SHEATH CELLS

CROSS REFERENCE TO RELATED APPLICATIONS

This patent application is a divisional of co-pending U.S. application Ser. No. 13/876,608 filed on Mar. 28, 2013, which is a U.S. national stage entry under 35 U.S.C. § 371 of International Patent Application No. PCT/JP2010/066999 filed on Sep. 29, 2010. The U.S. application Ser. No. 13/876,608 was published on Aug. 15, 2013, as US 2013/0212724 A1. The International Application was published in Japanese on Apr. 5, 2012, as International Publication No. WO 2012/042618 A1 under PCT Article 21(2).

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The sequence listings disclosed in the ASCII text file submitted herewith, named "seqlist.txt" and created on Mar. 7, 2016, the size of which is 1,726 bytes, are hereby incorporated by reference.

TECHNICAL FIELD

The present invention relates to a composition comprising dermal sheath (DS) cells expressing CD36 antigen (thrombospondin receptor) (to be referred to as "CD36-expressing DSc") and arbitrarily, dermal papilla (DP) cells (to be referred to as "DPc"), a method for regenerating hair follicles using such a composition, and an animal or three-dimensional skin model having hair follicles regenerated by such a method.

BACKGROUND ART

Hair is viewed to be extremely important in terms of aesthetic appearance. Thus, hair loss caused by congenital or acquired factors is a serious problem for many people. In today's society having a large elderly population and containing numerous sources of stress in particular, there are a growing number of opportunities for being at risk to the loss of scalp hair due to various acquired factors. In order to deal with this situation, various attempts have been made to provide superior hair tonics that more effectively demonstrate hair growth effects including the promotion of hair growth and thicker hair.

Hair follicles are exceptional organs that continue to repeatedly self-regenerate throughout nearly the entire life of a mature living organism. Elucidation of the mechanisms of this self-regeneration are expected to lead to clinical applications for which there are considerable demand, such as hair loss treatment using tissue or cell transplants, and the construction of natural and functionally superior skin sheets containing hair follicles and sebaceous glands. In recent years, research has progressed rapidly on follicular epithelial stem cells (epithelial cells) accompanying the growing interest in stem cell research, and the properties of dermal papilla cells, which are follicle-specific mesenchymal cells, have also been gradually determined. Dermal papilla cells fulfill the role of a so-called control tower that induces activation signals to follicular epithelial stem cells for self-regeneration of hair follicles, and have been determined, along with follicular epithelial stem cells, to be essential cells in follicle reconstruction evaluation systems (Kishimoto, et al., Proc. Natl. Acad. Sci. USA (1999), Vol. 96, pp. 7336-7341: Non-Patent Document 1).

Dermal papilla (DP) and dermal sheath (DS) surrounding the periphery of hair follicles both differ from epithelial cells composing the majority of hair follicles in that they are composed of mesenchymal-derived cell populations. With respect to DS, numerous findings have been reported in recent years suggesting its importance with respect to hair follicle formation. DS has been reported to be regenerated from DP in an experiment involving transplantation of hair bulbs-removed hair follicles of rat whiskers (1), and follicle regeneration has been reported to be induced in mice by transplanting DS of hair follicles from which the lower half has been severed (2). In addition, Jahoda, et al. (Development, 1992, April: 114(4), pp. 887-897: Non-Patent Document 2) reported that follicle regeneration can be induced by transplanting DS to humans (Horne, K. A. and Jahoda, C. A., Development, 1992, November: 116(3), pp. 563-571: Non-Patent Document 3). Moreover, the Tobin, Paus et al. group reported that cells migration occur between DS and DP, and that proliferation of dermal sheath cells (DSc) begins prior to DPc that begin to proliferate during the hair growth phase (Tobin, D. J. et al., J. Invest. Dermatol., 120, pp. 895-904, 2003: Non-Patent Document 4).

In this manner, although DS has a high possibility of fulfilling an important role in the formation of hair follicles, the mechanisms of action have not been well known, and even the properties of DSc are not understood. Therefore, we investigated the gene expression profile that characterizes DSc, and analyzed the properties for the purpose of clarifying the mechanism of action in the follicle formation.

PRIOR ART DOCUMENTS

Non-Patent Documents

Non-Patent Document 1: Kishimoto, et al., Proc. Natl. Acad. Sci. USA (1999), Vol. 96, pp. 7336-7341
Non-Patent Document 2: Jahoda, et al., Development, 1992, April: 114(4), pp. 887-897
Non-Patent Document 3: Horne, K. A. and Jahoda, C. A., Development, 1992, November: 116(3), pp. 563-571
Non-Patent Document 4: Tobin, D. J. et al., J. Invest. Dermatol., 120, pp. 895-904, 2003
Non-Patent Document 5: Linder, J. et al., Federation of American Societies for Experimental Biology, 14(2), 319 (2000)

SUMMARY OF THE INVENTION

Problems to be Solved by the Invention

An object of the present invention is to provide a novel follicle regeneration system.

Means for Solving the Problems

As a result of investigating the gene expression profile of DSc using a microarray, 304 genes were identified as genes with two or more higher expression rate in DSc in comparison with that in DPc and fibroblasts (FBc). As a result of categorizing these genes by function using GeneSpring's GeneOntology, many of the genes belonged to the category of vascular-related factors, thereby suggesting involvement between DS and blood vessels. Among these, DSc were found to highly express CD36, and this expression of CD36 by DSc was determined to be correlated with expression of HGF (hepatocyte growth factor) that demonstrates hair growth promotional effects (J. Linder, et al., Federation of American Societies for Experimental Biology, 14(2), 319 (2000): Non-Patent Document 5).

Thus, the present application includes the inventions indicated below.

[1] A composition for regenerating hair follicles, comprising CD36-expressing dermal sheath (DS) cells.

[2] The composition for regenerating hair follicles of [1], further comprising dermal papilla (DP) cells.

[3] The composition of [2], wherein the ratio of the number of CD36-expressing DSc to the number of DPc is about 10:1 to 1:10.

[4] The composition of [2] or [3], wherein the CD36-expressing DSc and the DPc are both derived from mice or both derived from rats.

[5] The composition of [2] or [3], wherein the CD36-expressing DSc and the DPc are heterologous cells, and each of them are derived from mice, rats or humans.

[6] A method for regenerating hair follicles, comprising transplanting the composition of any of [1] to [5] to a human.

[7] A method for regenerating hair follicles by transplanting the composition of any of [1] to [5] to a recipient animal.

[8] The method of [7], wherein the recipient animal is an immunosuppressed animal.

[9] The method of [7] or [8], wherein the recipient animal is an immunosuppressed animal selected from the group consisting of a nude mouse, SCID mouse and nude rat.

[10] A method for regenerating hair follicles, comprising producing a three-dimensional skin model containing the composition of any of [2] to [5].

[11] A chimeric animal imparted with regenerated hair follicles by transplanting the composition of any of [1] to [5] to a recipient animal.

[12] The chimeric animal of [11], wherein the recipient animal is an immunosuppressed animal.

[13] The chimeric animal of [11] or [12], wherein the recipient animal is an immunosuppressed animal selected from the group consisting of a nude mouse, SCID mouse and nude rat.

[14] A three-dimensional skin model imparted with regenerated hair follicles by producing a three-dimensional skin model containing the composition of any of [2] to [5].

Effects of the Invention

The hair follicle regeneration composition of the present invention can be used in transplant surgery for regenerating hair follicles and in research and development on hair follicle reconstruction.

EMBODIMENTS TO CARRY OUT THE INVENTION

Figure 1:
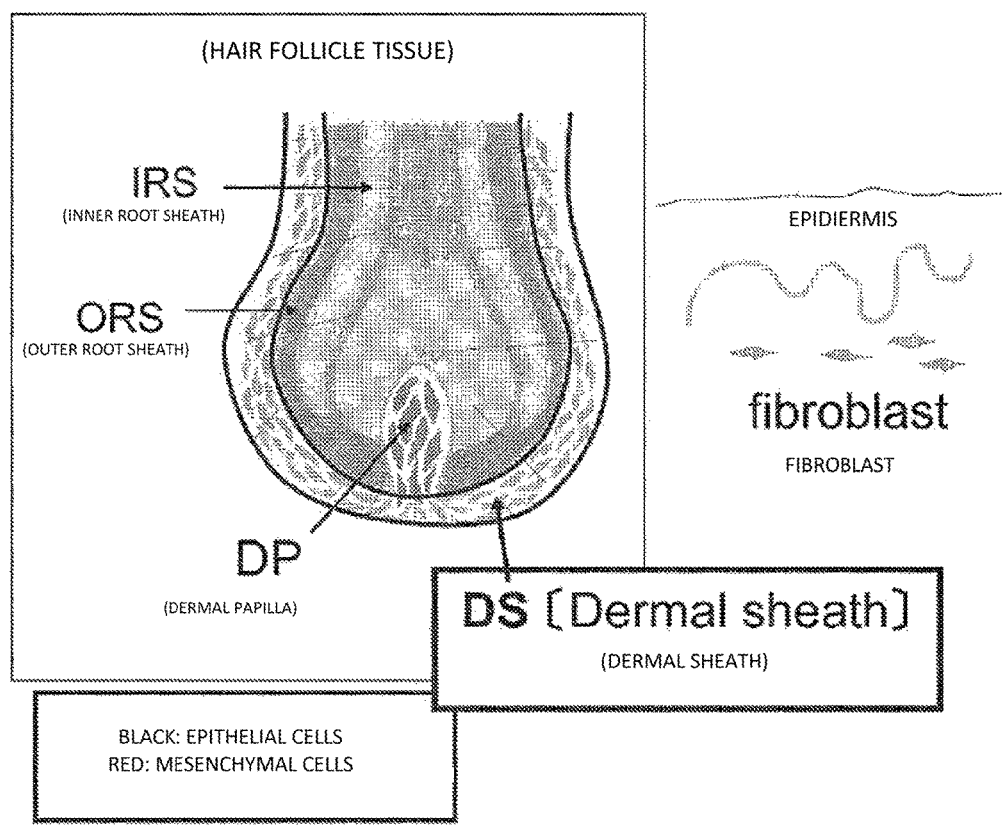
FIG. 1 is a schematic diagram showing the structure of hair follicle tissue.

The present invention provides a composition for regenerating hair follicles comprising DSc and arbitrarily comprising DPc, a method for regenerating hair follicles using such a composition, and an animal or three-dimensional skin model having hair follicles regenerated by such a method.

CD36 antigen is also referred to as thrombospondin receptor. CD36 is an integral membrane protein found on the surfaces of numerous cell types of vertebrate animals, and is also known as FAT, SCARB3, GP88, glycoprotein IV (gpIV) and glycoprotein IIIb (gpIIIb). CD36 is a member of the class B scavenger receptor family of cell surface proteins. In addition to thrombospondin, CD36 also binds with numerous other ligands such as collagen, erythrocytes parasitized by falciparum malaria parasites, oxidized low density lipoproteins, naturally-occurring lipoproteins, oxidized phospholipids and long-chain fatty acids. In recent research using genetically modified rodents, CD36 was able to be confirmed to fulfill a definite role in fatty acid and sugar metabolism, heart disease, sense of taste and the transport of vegetable fats and oils in the intestinal tract. CD36 can also be involved in impaired glucose tolerance, atherosclerosis, arterial hypertension, diabetes, cardiomyopathy and Alzheimer's disease.

Furthermore, the relationship between CD36 antigen and hair growth is completely unknown.

DSc are cells that compose the sheath portion that surrounds the periphery of DP in hair follicles, and are mesenchymal cells in the same manner as DPc. DP are considered to be derived from DS, and since DS proliferates prior to the proliferation of DP during the hair growth phase, DS is thought to supply DPc (Tobin, D. J. et al., J. Invest. Dermatol., 120, pp. 895-904, 2003: Non-Patent Document 4).

Although there are no particular limitations thereon, DSc that express CD36 can be sorted from DPc and other cells by, for example, commonly used cell sorting techniques using antibodies, and preferably monoclonal antibodies, to CD36.

The DSc of the present invention can be derived from the skin of all mammals, such as humans, chimpanzees, other primates, domestic animals such as dogs, cats, rabbits, horses, sheep, goats, cows or pigs, and experimental animals such as rats, mice or guinea pigs, and preferably nude mice, SCID mice or nude rats. In addition, the epidermal site may be a site where there is hair growth such as the scalp, or a site where there is no hair growth such as the foreskin.

DPc (dermal papilla cells) refer to cells that are mesenchymal cells located in the lowest portion of hair follicles, and fulfill the role of a so-called control tower by transducing activation signals to follicular epithelial stem cells for self-regeneration of hair follicles. Dermal papilla cell preparations containing only activated dermal papilla cells can be prepared according to, for example, the method described in Kishimoto, et al., Proc. Natl. Acad. Sci. USA (1999), Vol. 96, pp. 7336-7341 using transgenic mice. However, in consideration of yield and the like, these preparations are preferably prepared by, for example, preparing a cell suspension by treating a dermal tissue fraction, obtained by removing epidermal tissue from skin tissue, with collagenase, followed by destroying the follicular epithelial cells by subjecting the cell suspension to cryopreservation.

The above-mentioned cryopreservation method can be specifically carried out, for example, in the manner indicated below.

1. Mammalian skin is acquired.
2. The skin is then allowed to stand undisturbed for a suitable amount of time, such as overnight, in a protease solution such as a trypsin solution as necessary, the epidermal portion is subsequently removed with a forceps and the like, and the remaining dermis is treated with a collagenase to prepare a cell suspension.
3. The cell suspension is then filtered with a cell strainer as necessary, and the sediment is removed by allowing to stand undisturbed.
4. After measuring the number of cells, the cells are re-suspended in a cryopreservation solution at a suitable cell density such as $1\times10^5$/ml to $1\times10^8$/ml, and the suspension is dispensed into small aliquots as necessary and then placed in cryopreservation in accordance with ordinary cell storage methods.
5. The cells are stored for a suitable amount of time and used after thawing.

Although there are no particular limitations thereon, the freezing method consists of storing at a temperature of $-20°$ C. or lower, preferably $-50°$ C. or lower and more preferably $-80°$ C. or lower in an ultra-deep freezer, or in liquid nitrogen. Although there are no particular limitations on the duration of cryopreservation, it is a period of, for example, 1 day or more, preferably 3 days or more and more preferably 1 week or more to ensure that the epithelial cells are killed. Furthermore, dermal papilla cells have been confirmed to remain viable even after storing for 4 months in liquid nitrogen. An ordinary cryopreservation solution used to store cells, such as CellBanker 2 cryopreservation solution (Catalog No. BLC-2, Nippon Zenyaku Kogyo Co., Ltd.), can be used for the cryopreservation solution.

Measurement of the number of cells can be carried out by a method commonly known among persons with ordinary skill in the art. For example, the number of cells can be measured by placing a cell suspension obtained by diluting the cells with an equal volume of 0.4% Trypan blue stain (No. 15250-061, Invitrogen Corp.) on a hemocytometer (Eosinophil Counter, SLGC Co., Ltd.), and calculating the number of cells in accordance with the method described in the instruction manual provided with the hemocytometer.

Similar to DSc, the DPc of the present invention can be derived from the skin of all mammals, such as humans, chimpanzees, other primates, domestic animals such as dogs, cats, rabbits, horses, sheep, goats, cows or pigs, and experimental animals such as rats, mice or guinea pigs, and preferably nude mice, SCID mice or nude rats.

Preferably, the composition for regenerating hair follicles of the present invention further comprises epithelial cells. Epithelial cells are cells that compose the majority of the dermis or epidermis of skin, and arise from a single layer of basal cells in contact with the dermis. In using the example of mice, although epithelial cells derived from newborn mice (or fetuses) can be preferably used as epithelial cells, they may also be cells derived from mature skin, such as the epithelium of resting phase hair or epithelium of growth stage hair, or cultured cells in the form of keratinocytes. These cells can be prepared from the skin of a desired donor animal according to methods commonly known among persons with ordinary skill in the art.

In a preferable aspect thereof, the epithelial cells can be prepared in the manner described below.

1. Mammalian skin is acquired.
2. The epidermis of this skin is treated with trypsin by allowing to stand undisturbed overnight at 4° C. in PBS containing 0.25% trypsin as necessary.
3. After peeling off only the epidermal portion with a forceps and the like and slicing into thin sections, the epidermal tissue is treated by suspending for about 1 hour at 4° C. in a suitable culture broth (such as keratinocyte culture broth).
4. The suspension is passed through a cell strainer having a suitable pore size, followed by subjecting to centrifugal separation and recovering the epithelial cells.
5. The cell preparation is suspended in KGM or SFM medium at a desired cell density, and then allowed to stand undisturbed on ice until just before the time of use.

Similar to DSc and DPc, the epithelial cells of the present invention can be derived from the skin of all mammals, such as humans, chimpanzees, other primates, domestic animals such as dogs, cats, rabbits, horses, sheep, goats, cows or pigs, and experimental animals such as rats, mice or guinea pigs, and preferably nude mice, SCID mice or nude rats. In addition, the epidermal site may be a site where there is hair growth such as the scalp, or a site where there is no hair growth such as the foreskin.

Although there are no particular limitations on the ratio of DSc to DPc used, in the composition of the present invention, DSc and DPc are contained at a ratio of preferably 1:10 to 10:1, and more preferably 1:3 to 3:1. Moreover, epithelial cells are contained at a ratio to the total number of DSc and DPc of 1:10 to 10:1, preferably 1:1 to 10:1, more preferably 1:1 to 3:1 and most preferably 1:1.

The combination of DSc, DPc and arbitrarily epithelial cells may be from the same species or different species. Thus, the composition for regenerating hair follicles of the present invention may be, for example, a combination in which all of the DSc, DPc and epithelial cells are derived from a human, a combination in which all of the DSc, DPc and epithelial cells are derived from the same species of mammal other than human (the above combinations are combinations of the same species), a combination in which the DSc and DPc are derived from a human while the epithelial cells are derived a mammal other than human, a combination in which one of either the DSc or DPc are derived from a human, and the other and the epithelial cells are derived from the same species or different species of mammal other than a human, and a combination in which one of either the DSc or DPc are derived a mammal other than a human and the other and the epithelial cells are derived from a human (the above combinations are combinations of different species).

The method used to transplant the composition for regenerating hair follicles of the present invention into a recipient animal can be in accordance with a known transplant method. Reference can be made to, for example, Weinberg, et al., J. Invest. Dermatol., Vol. 100 (1993), pp. 229-236. For example, in the case of transplanting into nude mice, the cells that have been acquired are mixed just before or within 1 hour before transplant, the culture broth is removed by centrifugation (9000×g, 10 min.), and after forming a cell aggregate of about 50 µL, to 100 µL, the cell aggregate is promptly poured into a silicone dome-shaped chamber embedded in the skin on the backs of the nude mice. Two weeks later, the chamber is carefully removed and starting an additional 3 weeks later, the presence of hair formation at the transplant site can be observed macroscopically. Transplantation for the purpose of growing hair in animals including humans can be carried out by a similar method, and an appropriate method may be suitably determined by a physician or veterinarian.

In the case of transplanting the aforementioned composition into a recipient animal, that transplantation may be a homotransplantation, namely an autotransplantation, isotransplantation or allotransplantation, or may be a heterotransplantation. In the case of a homotransplantation, the dermal papilla cell preparation and the epithelial cells are from the same species as the recipient. In the case of a heterotransplantation, either the dermal papilla cell preparation or the epithelial cells are from a different species than the recipient while the other may be from the same species as the recipient, or both may be from a different species than the recipient. Examples of recipient animals include all mammals, such as humans, chimpanzees, other primates, domestic animals such as dogs, cats, rabbits, horses, sheep, goats, cows or pigs, and experimental animals such as rats, mice or guinea pigs, and preferably nude mice, SCID mice or nude rats.

In addition, a chimeric animal having regenerated hair follicles can be provided by transplanting the aforementioned composition according to the present invention into a suitable recipient animal. The resulting chimeric animal can serve as a useful animal model for, for example, researching and elucidating the mechanism of hair follicle regeneration, or screening drugs or herbs effective for regenerating hair follicles, growing hair or preventing hair loss. The recipient animal is preferably an immunosuppressed animal regardless of the source of each of the cells contained in system transplanted into the recipient animal. In addition, an animal species capable of being used as an experimental animal can be used for the animal species, and although any animal species may be used provided it coincides with the object of the present invention, preferable examples thereof include mice and rats. Among these animals, examples of immunosuppressed animals when using the example of mice include those in having the trait of a missing thymus in the manner of nude mice. Furthermore, in consideration of the object of the present invention, particularly preferable examples of recipient animals include commercially available nude mice (such as Balb-c nu/nu strain), SCID mice (such as Balb/c-SCID), and nude rats (such as F344/N Jcl-run).

Moreover, by incorporating the composition according to the present invention in a three-dimensional skin model, a three-dimensional skin model can be provided that has regenerated hair follicles. In this case, however, dermal papilla cells serving as a control tower for hair growth are essential. A three-dimensional skin model can be produced in the manner described below, for example, according to a method commonly known among persons with ordinary skill in the art (Amano, S. et al., Exp. Cell Res. (2001), Vol. 271, pp. 249-362). The three-dimensional skin model respectively contains DSc and DPc at $1\times10^6$ cells/cm$^2$ to $1\times10^8$ cells/cm$^2$, preferably at $1.0\times10^7$ cells/cm$^2$ to $1.5\times10^7$ cells/m$^2$, and more preferably at about $1.27\times10^7$ cells/cm$^2$.

Method for Producing Three-Dimensional Skin Model

A suitable number of human fibroblasts are dispersed in DMEM containing 0.1% collagen and 10% FBS followed by dispensing into a Petri dish and immediately allowing to stand undisturbed in a $CO_2$ incubator at 37° C. After the medium has gelled, the gel is scraped from the side walls and bottom of the Petri dish so as to suspend the gel in the Petri dish. The cells are then cultured while shaking the collagen gel to contract the gel to about one-fifth its original size and obtain a dermal model. The dermal model is then placed on a stainless steel grid, a glass ring is placed thereon, and 0.4 ml of cultured human epithelial cells ($1.0\times10^6$ cells/ml) dispersed in KGM (keratinocyte growth medium) are injected into the ring and cultured. At this time, DSc and DPc are simultaneously mixed and injected. Mouse neonatal epithelial cells can also be used instead of cultured human epithelial cells.

Medium consisting of DMEM, KGM, 5% FBS and $Ca^{2+}$ is placed in the Petri dish to a degree that the upper portion of the dermal model is exposed to air followed by culturing, and after about one week, the skin model is observed and assessed for the presence or absence of rudimentary hair follicle formation and regeneration.

Similar to the aforementioned chimeric animal having regenerated hair follicles, a three-dimensional skin model having regenerated hair follicles can be used for researching and elucidating the mechanism of hair follicle regeneration, or screening drugs or herbs effective for growing hair or preventing hair loss.

The following provides a more detailed explanation of the present invention by indicating examples thereof.

Example 1

(Method)

Cell Isolation and Culturing

Removal of the dermal portion of human scalp tissue was carried out with a scalpel in DMEM containing 10% fetal bovine serum (Gibco/Invitrogen Corp.), and hair follicles were extracted from the severed surface. Hair shafts containing outer root sheath cells (ORS, follicular epithelial cells) were removed from the hair follicles using microforceps so as to extract DP and DS. The isolated DP were static-cultured in a 35 mm collagen-coated tissue dish containing Medium-1 (Nissui low-serum fibroblast medium containing 10% fetal bovine serum, 10 ng/ml EGF, 20 ng/ml bFGF, 0.00075% β-mercaptoethanol, 100 units/ml (titer) penicillin, 0.1 mg/ml (titer) streptomycin and 0.25 μg/ml (titer) amphotericin B), while the isolated DS were treated with collagenase for 40 minutes at 37° C. followed by similarly static-culturing in a 35 mm collagen-coated tissue dish. After confirming the growth of both DP and DS one week later, the resulting DPc and DSc were used as experimental samples. Commercially available cells (Toyobo Co., Ltd.) were used for the fibroblasts (FBc). The DSc, DPc and FBc were static-cultured for 7 to 10 days using Medium-1. Subsequently, the cells were subcultured using trypsin. Culturing conditions consisted of culturing in a collagen-coated flask (T-75, Iwaki Glass Co., Ltd.) at 37° C. and 5% $CO_2$. In addition, each of the cells used in the experiment had been subcultured one to three times.

Normal human adult dermal microvascular endothelial cells (HMVEC, Kurabo Industries Ltd.) were used as vascular endothelial cells, and the cells were cultured in low-serum growth medium (Humedia-MvG, Kurabo Industries Ltd.) and then subcultured five times prior to use in the experiment.

Comparison of Gene Expression Profiles of DSc, DPc and FBc Using the Microarray Method Total RNA containing mRNA was collected from the DSc, DPc and FBc using the RNeasy Micro Kit (Qiagen Corp.). The collected RNA was subjected to double-stranded cDNA synthesis using Agilent's protocol followed by synthesis of cRNA labeled with cyanine 3.5. The labeled cRNA was hybridized for 17 hours at 65° C. on a microarray chip slide (Agilent, Whole Human Genome (4×44K), G4110) using a two-color assay. Comparisons of the gene expression levels of two types of cells each consisting of DSc and DPc, DPc and FBc and FBc and DSc were carried out on each chip slide using two types each of RNA derived from the DS of two individuals (total of 4 types), two types each of RNA derived from the DP of two individuals (total of 4 types), and two types each of RNA derived from the FB of one individual. After washing the slides, images of fluorescent signals (cyanine 3.5) of the cDNA on the chip were obtained with a dual-laser microarray scanner (Agilent Technologies Inc.). The image data was quantified using Feature Extraction Software Ver. 9.1, and at that time, taggings were made (tagged) to indicate abnormal values and low values at about the same level as background noise followed by analyzing the data. Each expression level was compared by comparing two sets of quantitative values of the acquired signals.

(Analysis of Microarray Data)

Gene Spring GX 7.3.1 software (Agilent Technologies Inc.) was used to analyze each gene expression level in greater detail using bioinformatics techniques. Abnormal values and low values at about the same level as background noise were tagged in a procedure using Feature Extraction Software Ver. 9.1, and analyses were conducted using those genes that were not tagged. The genes for which there was a difference in expression level between two types of cells were extracted and subjected to functional categorization by using GeneOntology (http://www.geneontology.org/). At that time, the degree of statistical significance was tested using Fisher's exact test.

Cell Staining

Cell staining using CD36 antibody consisted of seeding DSc in a four well-chamber slide (Nalgene, Nalge Nunc International Corp.) subjected to collagen surface treatment using an acidic collagen solution (Koken Co., Ltd.) and using the cells after culturing for 1 to 2 days. After washing with PBS, the cells were fixed for 30 minutes with 4% PFA, washed with PBS and treated for 10 minutes with PBS solution containing 0.1% Triton X-100. After blocking for 30 minutes with PBS containing 3% BSA, the cells were allowed to react for 1 hour with a primary antibody solution obtained by diluting CD36 antibody (ab17044, Abcam Inc.) 50-fold with PBS containing 1% BSA. After washing four times with PBS, the cells were allowed to react for 1 hour with a secondary antibody solution obtained by diluting Alexa 594-labeled anti-mouse IgG antibody (Invitrogen Corp.) 200-fold with PBS containing 1% BSA. After reacting with DAPI solution in order to carry out nuclear staining, the cells were washed four times with PBS and sealed with an anti-fade reagent (Prolong Gold Antifade Reagent, Invitrogen Corp.) and a cover glass. The cells were observed using a fluorescence microscope (Olympus Corp.).

Tissue Staining

Human scalp tissue was embedded in a frozen tissue embedding agent (OTC Compound, Sakura Finetek Japan Co., Ltd.), and frozen section slides were prepared with a frozen section production system (Cryostat, Leica Camera AG). After fixing for 15 minutes with 4% PFA, the tissue was washed with PBS and allowed to react for 1 hour using a blocking solution obtained by adding 5% skim milk, 1% donkey serum and 0.1% Triton X-100 to PBS. Next, the tissue was allowed to react for 1 hour at room temperature or overnight at 4° C. using a primary antibody solution obtained by diluting CD36 antibody solution (ab17044, Abcam Inc.) or CD31 antibody solution (AF806, R&D Co., Ltd.) 50-fold and 100-fold, respectively, with the blocking solution. Furthermore, CD31 antibody was used to label CD31 used as a vascular endothelial cell marker. After washing 3 times with PBS, the tissue was allowed to react for 1 hour at room temperature using a secondary antibody solution obtained by diluting Alexa 594-labeled anti-mouse IgG antibody (Invitrogen Corp.) or Alexa 488-labeled anti-rabbit IgG antibody (Invitrogen Corp.) 200-fold each with blocking solution. After reacting with DAPI solution, the tissue was washed 3 times with PBS and sealed with an anti-fade reagent (Prolong Gold Antifade Reagent) and a cover glass. The tissue was observed using a fluorescence microscope (Olympus Corp.).

Hair Follicle Whole-Mount Staining

Hair follicles isolated from human tissue were fixed while shake-culturing for 2 hours at 4° C. with 4% PFA. The follicles were sequentially subjected to dehydration treatment consisting of treating for 5 minutes each using 0.1% Tween PBS containing 25%, 50% or 75% ethanol (to be referred to as PBST) and treating for 5 minutes each using 100% ethanol. The treated samples were stored in ethanol at −20° C. At the time of use, after rehydrating with the same ethanol series PBST, the follicles were treated for 10 minutes with PBS containing 5% Triton X-100. Subsequently, the follicles were sequentially reacted with the blocking solution used for tissue staining, a primary antibody solution containing CD36 antibody (ab17044, Abcam Inc.) and CD31 antibody (AF806, R&D Co., Ltd.), a secondary antibody solution containing Alexa 594-labeled anti-mouse IgG antibody and Alexa 488-labeled anti-rabbit IgG antibody, and DAPI solution. Furthermore, the follicles were washed 8 times each using PBS containing 0.1% Triton X-100 both between the antibody reaction procedures and after staining. Reaction conditions consisted of reacting overnight at 4° C. in the case of the primary antibody solution, and reacting for 2 to 3 hours at 4° C. in the case of the secondary antibody solution. The follicles were observed with a fluorescence microscope (Olympus Corp.) after sealing with an anti-fade reagent (Prolong Gold Antifade Reagent) and a cover glass.

RT-PCR

RNA was collected from the cells using TRIzol (Invitrogen Corp.) in accordance with the protocol provided. The concentration of the collected RNA was measured with a nucleic acid quantification system (Nanodrop, Thermo Scientific Inc.). After making the concentrations of RNA targeted for comparison to a same level, cDNA was synthesized using oligo(dT) primers from the RNA using reverse transcriptase (Superscript III, Invitrogen Corp.) in accordance with the Invitrogen protocol. Quantitative RT-PCR was then carried out using the synthesized cDNA as template and using LightCycler® FastStart DNA MasterPLUS SYBR Green (Roche Diagnostics GmbH) for the reaction reagent and LightCycler (Roche Diagnostics GmBH) for the reaction device. Composition conditions were in accordance with the Roche protocol. PCR conditions consisted of initial denaturation for 10 minutes at 95° C., denaturation for 10 seconds at 95° C., annealing for 10 seconds at 60° C., and elongation for 10 seconds at 72° C. The primer data used is as indicated below.

```
G3PDH:
Forward primer:
                                          (SEQ ID NO: 1)
5'-GCACCGTCAAGGCTGAGAAC-3'

Reverse primer:
                                          (SEQ ID NO: 2)
5'-ATGGTGGTGAAGACGCCAGT-3'

CD36:
Forward primer:
                                          (SEQ ID NO: 3)
5'-GAGGAACTATATTGTGCCTATTCTTTGGC-3'
```

-continued

Reverse primer:
(SEQ ID NO: 4)
5'-CATAAAAGCAACAAACATCACCACACCAAC-3'

CD31:
Forward primer:
(SEQ ID NO: 5)
5'-ATGCCGTGGAAAGCAGATACTCTAG-3'

Reverse primer:
(SEQ ID NO: 6)
5'-AATTGCTGTGTTCTGTGGGAGCAG-3'

HGF:
Forward primer:
(SEQ ID NO: 7)
5'-GAGGGAAGGTGACTCTGAATGAG-3'

Reverse primer:
(SEQ ID NO: 8)
5'-AATACCAGGACGATTTGGAATGGCAC-3'

The expression levels of each gene were measured using the software provided. Furthermore, G3PDH was used as an internal standard, and this was used to correct the amount of cDNA of a control group when quantifying each gene.

Cell Sorting

The cells were sorted using the Cell Separation Magnet (BD Biosciences Inc.). Operating conditions were in accordance with the protocol provided by BD Biosciences Inc. After separating the cells using trypsin solution, the cell suspension was passed through a cell strainer having a pore size of 70 μm (Falcon Inc.) followed by counting the number of cells. 5 million to 10 million of cells were suspended in 500 ml of PBS solution containing 3% fetal bovine serum, followed by the addition of CD36 antibody (ab17044, Abcam Inc.) so as to be diluted 50-fold and allowing to react for about 15 minutes on ice. After recovering the cells by washing and centrifuging using 1×Imag Buffer (BD Biosciences Inc.), the cells were re-suspended in 30 μl of anti-mouse IgG1 magnetic particles (BD Biosciences Inc.) and allowed to stand undisturbed for 30 minutes on ice. 500 μl of 1×Imag Buffer (BD Biosciences Inc.) were added followed by placing in the Cell Separation Magnet (BD Biosciences Inc.) and allowing to stand undisturbed for 8 minutes. The supernatant was recovered while being careful so as not to dislodge cells adhered to the lateral surfaces by the magnet, and the resulting supernatant was used as CD36-negative DSc. Continuing, after again adding 500 μl of 1×Imag Buffer (BD Biosciences Inc.) and suspending cells adhered to the lateral surfaces, the suspension was placed in the Cell Separation Magnet and allowed to stand undisturbed for 4 minutes followed by removal of the supernatant. This procedure was further repeated once and the cells adhered to the lateral surfaces were used as CD36-positive DSc. The recovered CD36-positive and CD36-negative DSc were suspended in Medium-1 followed by culturing for 2 to 4 days at 37° C. and 5% $CO_2$ using a collagen-coated flask (T-25, Iwaki Glass Co., Ltd.) for the culture vessel, followed by use in the experiment.

Co-Culturing Experiment

An experiment was conducted using the CD36-positive and CD-36 negative DSc derived from each specimen for N=3 and 4 times, respectively. 300,000 of the sorted CD36-positive and CD36-negative DSc were respectively seeded to a collagen-coated flask (T-75). Subsequently, after culturing for 2 days in Medium-1, 400,000 HMVEC were added and co-cultured for 1 day in Humedica-MvG (Kurabo Industries Ltd.). Subsequently, the medium was replaced with medium obtained by adding 100 units/ml (titer) of penicillin, 0.1 mg/ml (titer) of streptomycin, 0.25 μg/ml (titer) of amphotericin B and 0.1% BSA (Sigma Corp.) to vascular endothelial cell basal medium (Humedia-EB2, Kurabo Industries Ltd.). After further co-culturing for 1 day, the cells were separated with trypsin solution followed by proceeding with analysis using FACS. The cells were then passed through a 70 μm cell strainer (Falcon Inc.), suspended in PBS solution containing 3% fetal bovine serum, and allowed to react for 20 minutes on ice using a primary antibody solution, i.e., CD31 antibody solution (AF806, R&D Co., Ltd.). After washing the cells with PBS solution containing 3% fetal bovine serum, the cells were allowed to react for 20 minutes on ice with secondary antibody solution, i.e., Alexa 488-labeled anti-rabbit IgG antibody (Invitrogen Corp.) and re-suspended in 0.5 ml of PBS solution followed by proceeding with analysis using Cell Lab Quanta SC (Beckman Coulter Inc.). Preparations, including laser accuracy management, were made using the protocol and working reagent designated by Beckman Coulter. The number of CD31-positive cells was measured using the FL1 channel (525 nm). Furthermore, correction was made to eliminate autofluorescence by using endothelial cells that did not react with CD31 antibody. Following measurement, the number of CD31-positive cells was calculated based on total number of cells obtained and the ratio of CD31-positive cells.

(Results)

Figure 2:
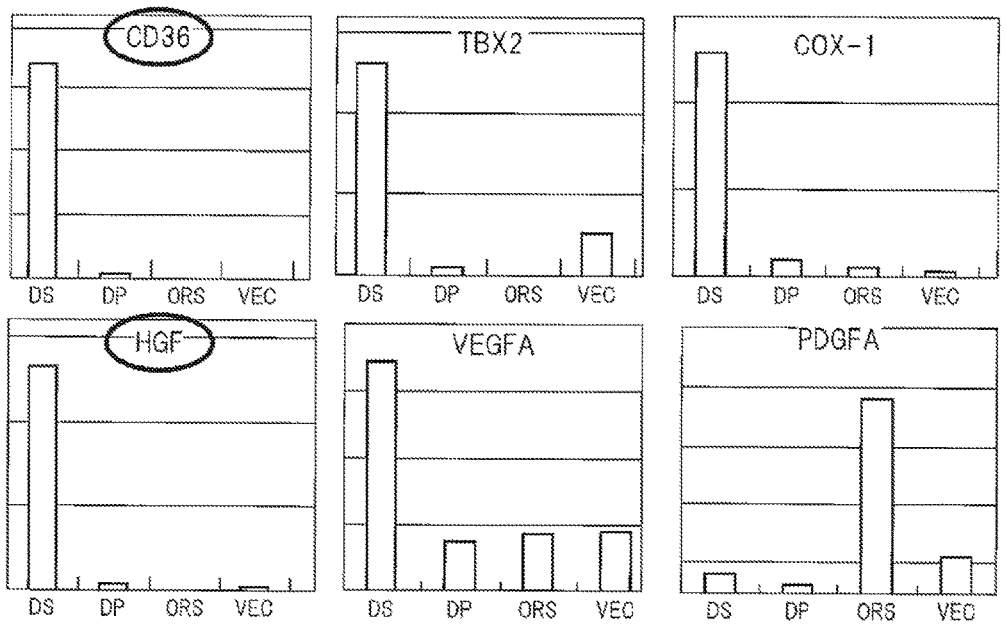
FIG. 2 indicates expression level of various types of vascular-related factors in various cells.

Table 1 shows the expression level of some vascular-related factors. Although vascular-related factors were determined to be highly expressed in DSs, CD36 and HGF were determined to be specifically highly expressed in DSs. FIG. 2 indicates the expression level of various types of vascular-related factors in DSc, DPc, ORS cells and VEC (vascular endothelial cells). CD36 and HGF were determined to be expressed extremely specifically in DS. On the basis of cell staining results as well, CD36-positive cells were observed to be present only in isolated DS cultured cells, while CD36-positive cells were determined to be absent in DPc or FBc (data not shown).

TABLE 1

Vascular-Related Factors Highly Expressed in DSc

|  | DS/DP | DS/FB | FB/DP |
|---|---|---|---|
| CD36 | 40.24 | 10.97 | 3.93 |
| HGF | 20.19 | 3.28 | 10.34 |
|  | 14.52 | 4.33 | 4.45 |
|  | 17.85 | 4.14 | 4.47 |
| TBX2 (T-box2 (transcription factor)) | 20.67 | 4.68 | 6.07 |
| VEGFA (vascular endothelial cell growth factor) | 3.41 | 5.12 | 0.50 |
|  | 4.34 | 7.40 | 0.48 |
|  | 2.22 | 4.16 | 0.52 |
|  | 2.68 | 4.55 | 0.60 |
| PDGFA (platelet-derived growth factor) | 5.82 | 3.67 | 1.80 |
| COX-1 (prostaglandin synthase) | 11.73 | 2.24 | 4.88 |
|  | 9.64 | 1.60 | 5.83 |

Figure 3:
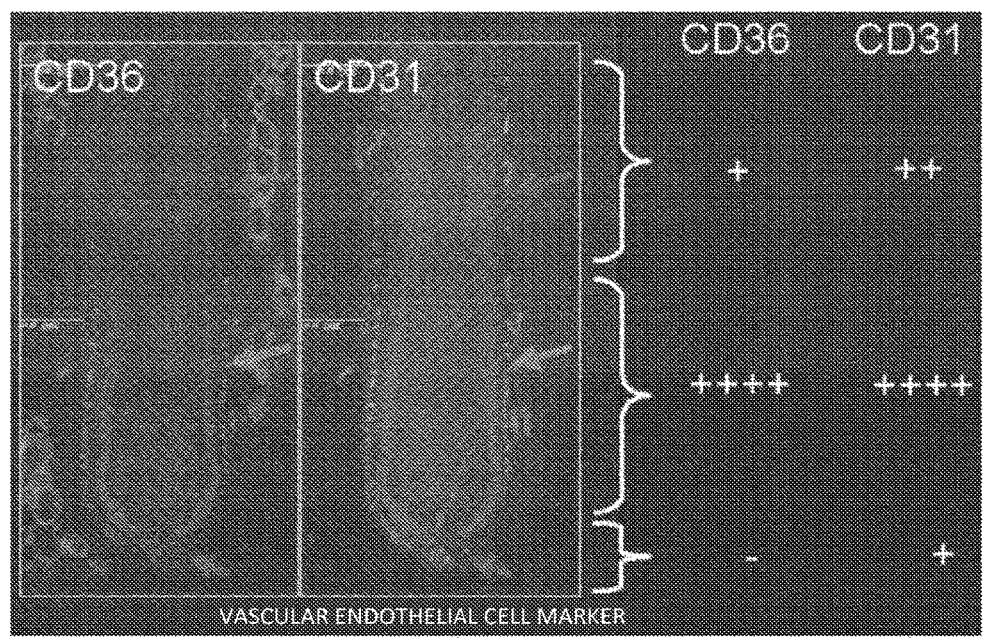
FIG. 3 is an image obtained by CD36 and CD31 immunohistochemical staining.
Figure 4:
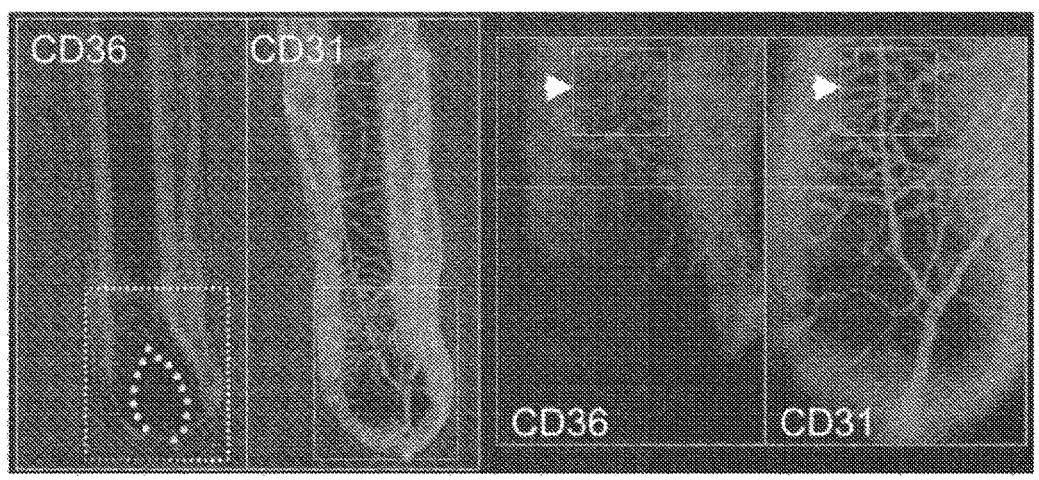
FIG. 4 is an image of whole mount stained hair follicles obtained by CD36 and CD31 immunostaining.

Specific staining of CD36 was also observed in the dermal sheaths of hair follicles, namely DS as a result of immunohistochemical staining of CD36 and CD31 on the sections of hair follicle (FIG. 3). Moreover, the results of hair follicle whole-mount staining indicated dense areas of blood vessels in a portion of the DS, and CD36-positive DSc were determined to be localized in those dense areas. Thus, CD36-positive DSc was suggested to be intimately involved with blood vessels. In addition, although CD36-positive DSc cells are nearly always co-localized with blood vessels, CD36-positive DSc are absent in the vicinity of some vessels (FIG. 4).

Thus, CD36-positive DSc cells were suggested to promote vascularization by, for example, promoting the proliferation of vascular endothelial cells.

Figure 5:
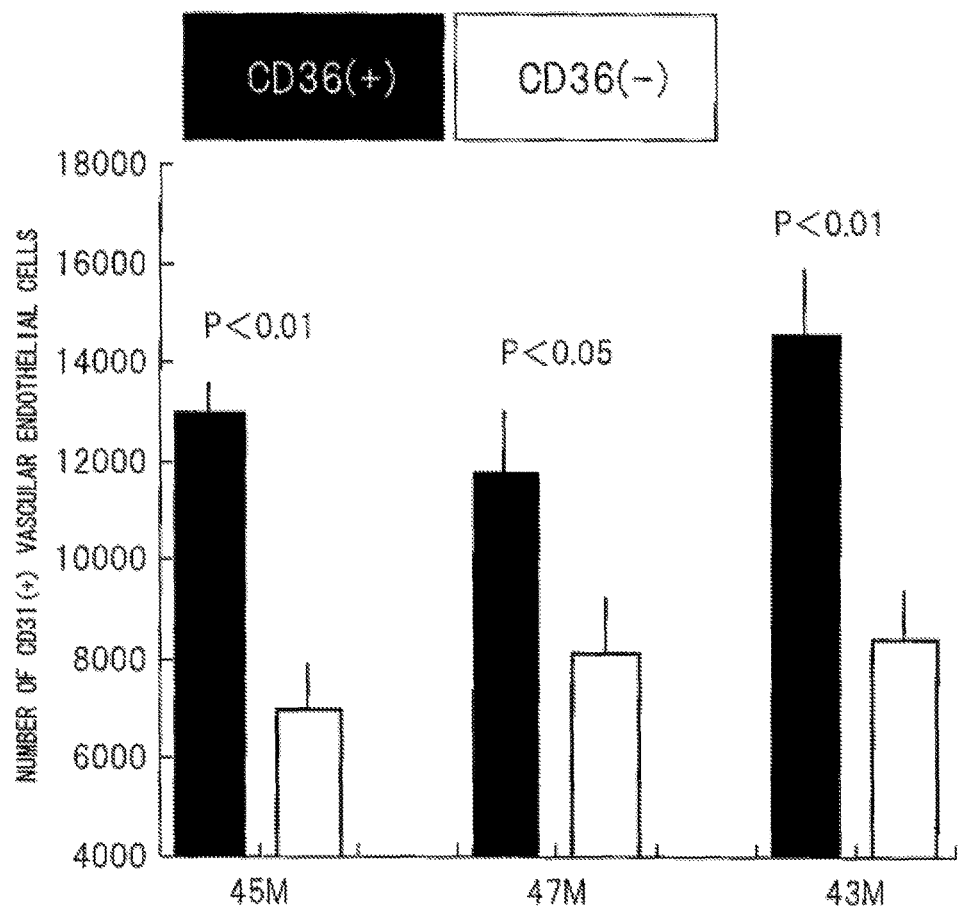
FIG. 5 indicates the results of co-culturing CD36-positive DSc and vascular endothelial cells.
Figure 6:
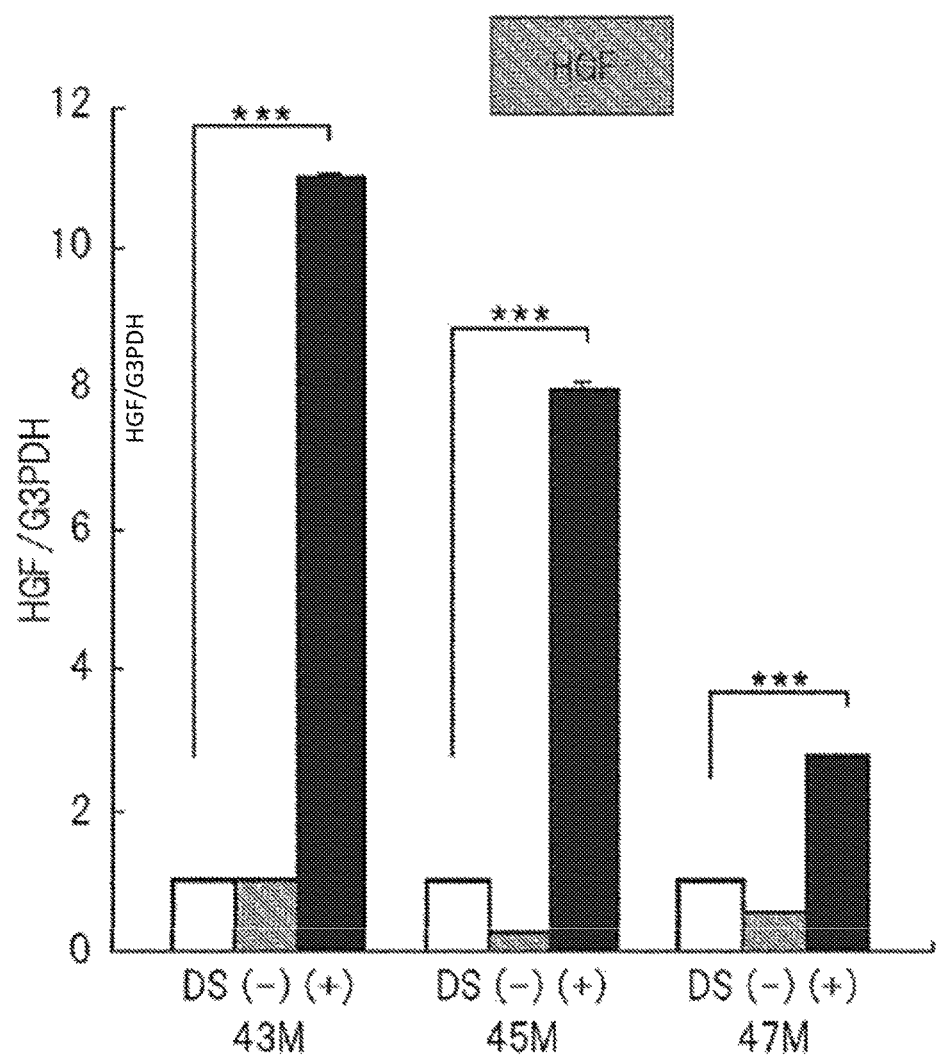
FIG. 6 indicates the results of HGF expression level in CD36-positive DSc.

In an experiment in which CD36-positive DSc isolated by cell sorting were co-cultured with vascular endothelial cells, the CD36-positive DSc were indicated to significantly promote the proliferation of vascular endothelial cells in comparison with CD36-negative DSc (FIG. 5). Moreover, isolated CD36-positive DSc were also indicated to highly express HGF in comparison with CD36-negative DSc cells (FIG. 6). As mentioned above, HGF is commonly known as a factor that promotes the growth of new hair and hair growth (Non-Patent Document 5). Thus, transplantation of CD36-positive DSc into hair follicles is clearly effective for the growth of new hair and hair growth.

The invention claimed is:

1. A method for regenerating hair follicles, comprising the step of transplanting a composition comprising CD36-expressing human dermal sheath cells to human skin, wherein the hair follicles are regenerated.

2. The method of claim 1, wherein said composition is prepared by a process comprising the step of sorting CD36-expressing human dermal sheath cells from a human hair follicle tissue by use of a cell sorting technique using an antibody to CD36.

3. The method of claim 2, wherein said composition further comprises human dermal papilla cells.

4. The method of claim 3, wherein the ratio of the number of said CD36-expressing human dermal sheath cells to the number of said human dermal papilla cells is about 10:1 to 1:10.

5. The method of claim 1, wherein said composition further comprises human dermal papilla cells.

6. The method of claim 5, wherein the ratio of the number of said CD36-expressing human dermal sheath cells to the number of said human dermal papilla cells is about 10:1 to 1:10.

7. A method for regenerating hair follicles, comprising the steps of:

preparing a composition comprising CD36-expressing human dermal sheath cells; and transplanting said composition to human skin, wherein the hair follicles are regenerated.

8. The method of claim 7, wherein said composition is prepared by a process comprising the step of sorting CD36-expressing human dermal sheath cells from a human hair follicle tissue by use of a cell sorting technique using an antibody to CD36.

9. The method of claim 8, wherein said composition further comprises human dermal papilla cells.

10. The method of claim 9, wherein the ratio of the number of said CD36-expressing human dermal sheath cells to the number of said human dermal papilla cells is about 10:1 to 1:10.

11. The method of claim 7, wherein said composition further comprises human dermal papilla cells.

12. The method of claim 11, wherein the ratio of the number of said CD36-expressing human dermal sheath cells to the number of said human dermal papilla cells is about 10:1 to 1:10.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: G3PDH Forward Primer

<400> SEQUENCE: 1
gcaccgtcaa ggctgagaac                                              20

<210> SEQ ID NO 2
<211> LENGTH: 20
<212> TYPE: DNA
<213> ORGANISM: Artificial Sequence
<220> FEATURE:
<223> OTHER INFORMATION: G3PDH Reverse Primer

<400> SEQUENCE: 2
atggtggtga agacgccagt                                              20

<210> SEQ ID NO 3
<211> LENGTH: 29
<212> TYPE: DNA
<213> ORGANISM: Artificial Sequence
<220> FEATURE:
<223> OTHER INFORMATION: CD36 Forward Primer

<400> SEQUENCE: 3
gaggaactat attgtgccta ttctttggc                                    29

<210> SEQ ID NO 4
<211> LENGTH: 30
<212> TYPE: DNA
<213> ORGANISM: Artificial Sequence
<220> FEATURE:
<223> OTHER INFORMATION: CD36 Reverse Primer

<400> SEQUENCE: 4
cataaaagca acaaacatca ccacaccaac                                   30

<210> SEQ ID NO 5
<211> LENGTH: 25
<212> TYPE: DNA
<213> ORGANISM: Artificial Sequence
<220> FEATURE:
<223> OTHER INFORMATION: CD31 Forward Primer

<400> SEQUENCE: 5
atgccgtgga aagcagatac tctag                                        25

<210> SEQ ID NO 6
<211> LENGTH: 24
<212> TYPE: DNA
<213> ORGANISM: Artificial Sequence
```

```
<220> FEATURE:
<223> OTHER INFORMATION: CD31 Reverse Primer

<400> SEQUENCE: 6
aattgctgtg ttctgtggga gcag                                              24

<210> SEQ ID NO 7
<211> LENGTH: 23
<212> TYPE: DNA
<213> ORGANISM: Artificial Sequence
<220> FEATURE:
<223> OTHER INFORMATION: HGF Forward Primer

<400> SEQUENCE: 7
gagggaaggt gactctgaat gag                                               23

<210> SEQ ID NO 8
<211> LENGTH: 26
<212> TYPE: DNA
<213> ORGANISM: Artificial Sequence
<220> FEATURE:
<223> OTHER INFORMATION: HGF Reverse Primer

<400> SEQUENCE: 8
aataccagga cgatttggaa tggcac                                            26
```